US006913895B1

(12) United States Patent
Goldman et al.

(10) Patent No.: US 6,913,895 B1
(45) Date of Patent: Jul. 5, 2005

(54) METHODS FOR ASSAYING TRANSGLYCOSYLASE REACTIONS, AND FOR IDENTIFYING INHIBITORS THEREOF (75) Inventors: Robert C. Goldman, West Windsor, NJ (US); Arthur A. Branstrom, Hightstown, NJ (US)

(73) Assignee: Advanced Medicine East, Inc., South San Francisco, CA (US)

( * ) Notice: Subject to any disclaimer, the term of this patent is extended or adjusted under 35 U.S.C. 154(b) by 0 days.

(21) Appl. No.: 09/375,851

(22) Filed: Aug. 17, 1999

(51) Int. Cl.$^7$ .................... C12Q 1/70; C12Q 1/00; G01N 33/567; G01N 33/573; G01N 33/53

(52) U.S. Cl. .................... 435/7.32; 435/4; 435/5; 435/7.2; 435/7.4; 435/7.6; 435/7.71; 435/7.72; 435/7.91; 435/7.15; 435/183; 435/220

(58) Field of Search ............... 435/7.2, 7.32, 435/7.4, 7.91, 15, 21, 24, 29, 41, 69.2, 173.1, 183, 243, 283.1; 436/504, 807, 815

(56) References Cited

U.S. PATENT DOCUMENTS 4,687,732 A 8/1987 Ward et al.
5,681,694 A 10/1997 Hoskins et al.

OTHER PUBLICATIONS

Allen, N. E. et al., "Molecular interactions of a semisynthetic glycopeptide antibiotic with D–alanyl–D–alanine and D–alanyl–D–lactate residues," *Antimicrob. Agents Chemother.*, 1997, 41(1), 66–71.

Allen, N.E. et al., "Inhibition of Peptidoglycan Biosynthesis in Vancomycin–Susceptible and –Resistant Bacteria by a Semisynthetic Glycopeptide Antibiotic," *Antimicrob. Agents and Chemotherapy*, 1996, 41(10), 2356–2362.

Arthur, M. et al., "Mechanisms of glycopeptide resistance in enterococci," *J. Infect.*, 1996, 32, 11–16.

Broker, T. R. et al, "Electron microscopic visualization of tRNA genes with ferritin–avidin: biotin labels," *Nucleic Acids Research*, 1978, 5(2), 363–384.

Denome, S. A. et al., "*Escherichia coli* mutants lacking all possible combinations of eight penicillin binding proteins: viability, characteristics, and implications for peptidoglycan synthesis," *J. Bacteriol.*, 1999, 181(13), 3981–3993.

Di Berardino, M. et al., "The monofunctional glycosyltransferase of *Escherichia coli* is a member of a new class of peptidoglycan–synthesising enzymes," *FEBS Lett.*, 1996, 392(2), 184–188.

El–Abadla, N. et al., "Meonomycin A: The role of the methyl group in the moenuronamide unit and a general discussion of structure–activity relationships," *Tetrahedron*, 1999, 55, 699–722.

Ge, M. et al., "Vancomycin derivatives that inhibit peptidoglycan biosynthesis without binding D–Ala–D–Ala," *Science*, 1999, 284, 507–511.

Hara, H. et al., "A novel glycan polymerase that synthesizes uncross–linked peptidoglycan in *Escherichia coli*," *FEBS Letts.*, 1984, 168(2), 155–160.

Ishino, F. et al., "Peptidoglycan synthetic enzyme activities of highly purified penicillin– binding protein 3 in *Escherichia coli*: a septum–forming reaction sequence," *Biochem. Biophys. Res. Commun.*, 1981, 101(3), 905–911.

(Continued)

Primary Examiner—Lynette R. F. Smith
Assistant Examiner—J. Hines
(74) Attorney, Agent, or Firm—Woodcock Washburn LLP (57) ABSTRACT

This invention relates to the field of bacterial transglycosylase reactions. The invention is directed to methods for assaying for transglycosylase activity, methods of identifying inhibitors of transglycosylase activity, inhibitors identified by such methods, and methods of identifying the stage of inhibition at which such inhibitors act.

9 Claims, 3 Drawing Sheets

OTHER PUBLICATIONS

Ishino, F. et al., "Dual enzyme activities of cell wall peptidoglycan synthesis, peptidoglycan transglycosylase and penicillin–sensitive transpeptidase, in purified preparations of *Escherichia coli* penicillin–binding protein 1A," *Biochem. Biophys. Res. Commun.*, 1980. 97(1), 287–293.

Ishino, F. et al., "Peptidoglycan synthetic activities in membranes of *Escherichia coli* caused by overproduction of penicillin–binding protein 2 and rodA protein," *J. Biol. Chem.*, 1986, 261(15), 7024–7031.

Langer, P. R. et al., "Enzymatic synthesis of biotin–labeled polynucleotides: Novel nucleic acid affinity probes," *Proc. Natl. Acad. Sci. USA*, 1981, 78(11), 6633–6637.

Leclercq, R., "Les Glycopeptides: mécanismes d'action et de résistance," *La Presse Médicale*, 1999, 28(13), 720–721 (English language translation provided).

Leclercq, R. et al., "Resistance to glycopeptides in enterococci," *Clin. Infect. Dis.*, 1997, 24, 545–554.

Malabarba, A. et al., "Structural modifications of glycopeptide antibiotics," *Med. Res. Rev.*, 1997, 17, 69–137.

Manning et al., "A Method for Gene Enrichment Based on the Avidin–Biotin Interaction. Application to the *Drosophila* Ribosomal RNA Genes," *Biochemistry*, 1977, 16(7), 1364–1370.

Manning et al., "A New Method of in situ Hybridization," *Chromosoma*, 1975, 53, 107–117.

Matsuhashi, M. 1994, "Utilization of lipid linked precursors and the formation of peptidoglycan in the process of cell growth and division: Membrane enzymes involved in the final steps of peptidoglycan synthesis and the mechanism of their regulation," in *Bacterial Cell Wall: New Comprehensive Biochemistry*, Ghuysen, J.–M. et al. (eds.), Elsevier, New York. 1994, vol. 27, 55–71.

Nagarajan, R., "Structure–activity relationships of vancomycin–type glycopeptide antibiotics," *J. Antibiot (Tokyo)*, 1993, 46, 1181–1195.

Paik, J. et al., "Mutational analysis of the *Streptococcus pneumoniae* bimodular class A penicillin–binding proteins," *J. Bacteriol.*, 1999, 181(12), 3852–3856.

Park, W. et al., "Major peptidoglycan transglycosylase activity in *Streptococcus pneumoniae* that is not a penicillin binding protein," *FEMS Microb. Lett.*, 1985, 27, 45–48.

Park, W. et al., "*Staphylococcus aureus* and *Micrococcus luteus* peptidoglycan transglycosylases that are not penicillin–binding proteins," *J. Bacteriol.*, 1984, 157(2), 538–544.

Schiffer, G. et al., "Cloning and biochemical characterization of the bifunctional penicillin–binding protein 1C from *Escherichia coli*," *J. Biol. Chem.*, 1999, 274(45), 32031–32039.

Sharma, U. K. et al., "Expression and characterization of the ponA (ORF 1) gene of *Haemophilus influenzae*: functional complementation in a heterologous system," *J. Bacteriol.*, 1995, 177(23), 6745–6750.

Sodja, A. et al., "Gene mapping and gene enrichment by the avidin–biotin interaction: use of cytochrome–c as a polyamine bridge," *Nucleic Acids Research*, 1978, 5(2), 385–401.

Spratt, B. G. et al., "Microcorrespondence: Monofunctional biosynthetic peptidoglycan transglycosylases," *Mol. Microbiol.*, 1996, 19(3), 639–640.

Suzuki, H. et al., "In vitro peptidoglycan polymerization catalysed by penicillin binding protein 1b of *Escherichia coli* K–12," *FEBS Lett.*, 1980. 110(2), 245–249.

Taku, A. et al., "Purification of the peptidoglycan transglycosylase of *Bacillus megaterium*," *J. Biol. Chem.*, 1982, 257(9), 5018–5022.

van Heijenoort, Y. et al., "Polymerization by transglycosylation in the biosynthesis of the peptidoglycan of *Escherichia coli* K 12 and its inhibition by antibiotics," *FEBS Lett.*, 1978, 89(1), 141–144.

van Heijenoort, Y. et al., "Biosynthesis of the peptidoglycan of *Escherichia coli* K–12: properties of the in vitro polymerization by transglycosylation," *FEBS Lett.*, 1980, 110(2), 241–244.

van Heijenoort, Y. et al., "Membrane intermediates in the peptidoglycan metabolism of *Escherichia coli*: possible roles of PBP 1b and PBP 3," *J. Bacteriol.*, 1992, 174(11), 3549–3557.

van Heijenoort, Y. et al., ERRATA: "Membrane intermediates in the peptidoglycan metabolism of *Escherichia coli*: possible roles of PBP 1b and PBP 3," *J. Bacteriol.*, 1992, 174(11), 6004.

Wada, A. et al., "Penicillin–binding protein 1 of *Staphylococcus aureus* is essential for growth," *J. Bacteriol.*, 1998, 180(10), 2759–2765.

Walsh, C.T. et al., "Bacterial resistance to vancomycin: five genes and one missing hydrogen bond tell the story," *Chem. Biol.*, 1996, 3, 21–28.

Walsh, C.T., "Vancomycin resistance: decoding the molecular logic," *Science*, 1993, 261, 308–309.

Walsh, C.T., Corrections and Clarifications: "Vancomycin resistance: decoding the molecular logic," Science, 1993, 261(5131), 164.

Williams, D.H., "The glycopeptide story—how to kill the deadly 'superbugs'," *Nat. Prod. Rep.*, 1996, 13, 469–477.

Zijderveld, C. A. et al., "Hybrid proteins of the transglycosylase and the transpeptidase domains of PBP1B and PBP3 of *Escherichia coli*," *J. Bacteriol.*, 1995, 177(21), 6290–6293.

U.S. Appl. No. 09/241,862.

Tanaka, H. et al., "Studies on bacterial cell wall inhibitors. II. Inhibition of peptidoglycan synthesis in vivo and in vitro by amphomycin," *Biochim Biophys Acta*,Netherlands, 1977, 497 (3), 633–640.

Zemel, R.I., et al., "Pyruvate–uridine diphospho–N–acetylglucosamine transferase. Purification to homogeneity and feedback inhibition," *J. Biol Chem*, 1975, 250(8), 3185–92.

METHODS FOR ASSAYING TRANSGLYCOSYLASE REACTIONS, AND FOR IDENTIFYING INHIBITORS THEREOF

FIELD OF THE INVENTION

This invention relates to the field of bacterial transglycosylase reactions. The invention is directed to methods for assaying for transglycosylase activity, methods of identifying inhibitors of transglycosylase activity, inhibitors identified by such methods, and methods of identifying the stage of inhibition at which such inhibitors act.

BACKGROUND OF THE INVENTION

Polymerization of biosynthetic intermediates into bacterial peptidoglycan is essential for growth and survival of bacterial cells, and thus represents a novel target for discovery and design of new antibacterial compounds for clinical use. Bacterial cell wall synthesis requires a functional transglycosylation system in order to polymerize cell wall intermediates into peptidoglycan. The biochemical pathway of peptidoglycan synthesis in bacteria initiates in the cytoplasm with the synthesis of two key nucleotide-linked intermediates, UDP-N-acetyl-muramyl-peptide ("UDP-MurNAc-peptide", or "MurNAc") and UDP-N-acetylglucosamine ("UDP-GlcNAc", or "GlcNAc"). UDP-MurNAc-peptide (which may be in the form of UDP-MurNAc-pentapeptide or UDP-MurNAc-tetrapeptide) is transferred via the MraY protein to a C55 undecaprenol phosphate carrier lipid, thereby generating MurNAc-pentapeptide-pyrophosphoryl-undecaprenol ("lipid I"). N-acetylglucosamine is then transferred to lipid I by the MurG enzyme, generating N-acetylglucosamine-β-1,4-MurNAc-pentapeptide-pyrophosphoryl-undecaprenol ("lipid II"). Lipid II is then polymerized into peptidoglycan by specific transglycosylases.

Presently available methods for assaying transglycosylase activity rely on exogenously supplied substrate, and thus require laborious purification procedures that yield only small amounts of substrate for use in measuring enzymatic activity. In addition, the chemical state of the isolated substrate is difficult to monitor and control, leading to variable activity for the isolated substrate. Thus the ability to detect and characterize inhibitors of the transglycosylation reaction by screening large numbers of compounds for chemical and natural product inventories is not feasible. Furthermore, the lack of available methods for assaying transglycosylase activity directly renders it difficult to distinguish among inhibitors which exert their inhibitory effects at different stages of the peptidoglycan synthesis pathway.

The known transglycosylases are either monofunctional or bifunctional enzymes. Bifunctional enzymes comprise a domain for catalyzing the transglycosylation reaction and a domain catalyzing the transpeptidation reaction cross-linking nascent peptidoglycan to the pre-existing peptidoglycan, while monofunctional transglycosylase enzymes lack a transpeptidase domain. The bifunctional class is also referred to as penicillin-binding-proteins ("PBPs"), due to the fact that the transpeptidase domain can bind penicillin. Examples of this class of bifunctional PBPs are PBP1A, 1B, 2, and 3 from *E. coli*. Matsuhashi, M. 1994, *Utilization of lipid linked precursors and the formation of peptidoglycan in the process of cell growth and division: Membrane enzymes involved in the final steps of peptidoglycan synthesis and the mechanism of their regulation*, pp. 55–72. In J.-M. Ghuysen and R. Hakenbeck (ed.), *Bacterial Cell Wall: New Comprehensive Biochemistry*, vol. 27. Elsevier, N.Y. Matsuhashi et al. suggest that the ability to directly measure transglycosylase activity may depend on the form of the lipid II substrate and precise reaction conditions. In addition, they suggest that PBP2 and PBP3 may require the accessory proteins RodA and FtsW, respectively, for maximal activity. PBP1C was recently identified in the complete *E. coli* genome sequence, and appears to represent a new, bifunctional enzyme. Schiffer, G., M. Templin, and J. Holtje, 1997, *Cloning and biochemical characterization of the bifunctional penicillin-binding protein 1 C from Escherichia coli*, GenBank: accession no. U88571.

Monofunctional transglycosylases also exist in bacteria. These enzymes lack a transpeptidase domain, but these enzymes have the ability to synthesize uncrosslinked peptidoglycan in vitro. The presence of monofunctional transglycosylases is not unique to *E. coli*. *Nisseria gonorrhoeae*, *Haemophilus influenzae*, and *Klebsiella pneumoniae*, all appear to contain genes for monofunctional transglycosylases, as do *Staphylococcus aureus* and *Alcaligenes eutrophus*. Spratt, B. G., J. Zhou, M. Taylor, and M. J. Merrick, 1996, *Monofunctional biosynthetic peptidoglycan transglycosylases*, Mol Microbiol. 19(3):639–40; Di Berardino, M., A. Dijkstra, D. Stuber, W. Keck, and M. Gubler, 1996, *The monofunctional glycosyltransferase of Escherichia coli is a member of a new class of peptidoglycan-synthesising enzymes*. FEBS Lett. 392(2):184–8. In addition, *Bacillus megaterium*, *Staphylcoccus aureus* and *Micrococcus luteus*, and *Streptococcus pneumoniae*, exhibit monofunctional transglycosylase activity. Taku, A., M. Stuckey, and D. P. Fan, 1982, *Purification of the peptidoglycan transglycosylase of Bacillus megaterium*, J Biol Chem. 257(9):5018–22; Park, W., and M. Matsuhashi, 1984, *Staphylococcus aureus and Micrococcus luteus peptidoglycan transglycosylases that are not penicillin-binding proteins*, J Bacteriol. 157(2):538–44; Park, W., H. Seto, R. Hakenbach, and M. Matsuhashi, 1985, *Major peptidoglycan transglycosylase activity in Streptococcus pneumoniae that is not a penicillin binding protein*, FEMS Microb. Lett. 27:45–48. The role that these enzymes play in cellular peptidoglycan synthesis is not presently known. The essential nature and roles of several high molecular weight PBPs have been investigated by mutational analysis. The most recent study created *E. coli* mutants lacking all possible combinations of eight PBPs, and confirmed the need for at least PBP1A or 1B for growth. Denome, S. A., P. K. Elf, T. A. Henderson, D. E. Nelson, and K. D. Young, 1999, *Escherichia coli mutants lacking all possible combinations of eight penicillin binding proteins: viability, characteristics, and implications for peptidoglycan synthesis*, J Bacteriol. 181(13):3981–93. *S. pneumoniae* contains six identified PBPs, and expression of PBP1A or 2A is required for growth. Paik, J., I. Kern, R. Lurz, and R. Hakenbeck, 1999, *Mutational analysis of the streptococcus pneumoniae bimodular class A penicillin-0117 binding proteins* [In Process Citation]. J Bacteriol., 181(12):3852–6. The pbpA gene, encoding PBP 1 in *Staphylococcus aureus* appears to be essential for growth. Wada, A., and H. Watanabe, 1998, *Penicillin-binding protein 1 of Staphylococcus aureus is essential for growth*, J Bacteriol. 180(10):2759–65.

The initial assays developed to measure transglycosylase activity required purification of radiolabeled, native lipid II from bacterial cells. See, e.g., Ishino, F., and M. Matsuhashi, 1981, *Peptidoglycan synthetic enzyme activities of highly purified penicillin-binding protein 3 in Escherichia coli: a* septum-forming reaction sequence, Biochem Biophys Res Commun., 101(3):905–11; Ishino, F., K. Mitsui, S. Tamaki, and M. Matsuhashi, 1980, *Dual enzyme activities of cell wall peptidoglycan synthesis, peptidoglycan transglycosylase and penicillin-sensitive transpeptidase, in purified preparations of Escherichia coli penicillin-binding protein 1A,* Biochem Biophys Res Commun. 97(1):287–93; Ishino, F., W. Park, S. Tomioka, S. Tamaki, I. Takase, K. Kunugita, H. Matsuzawa, S. Asoh, T. Ohta, B. G. Spratt, et al., 1986, *Peptidoglycan synthetic activities in membranes of Escherichia coli caused by overproduction of penicillin-binding protein 2 and rodA protein,* J Biol Chem. 261(15):7024–31; Suzuki, H., Y. van Heijenoort, T. Tamura, J. Mizoguchi, Y. Hirota, and J. van Heijenoort, 1980, *In vitro peptidoglycan polymerization catalysed by penicillin binding protein 1b of Escherichia coli K-12,* FEBS Lett. 110(2):245–9, Van Heijenoort, Y., M. Derrien, and J. Van Heijenoort, 1978, *Polymerization by transglycosylation in the biosynthesis of the peptidoglycan of Escherichia coli K 12 and its inhibition by antibiotics,* FEBS Lett. 89(1):141–4; van Heijenoort, Y., and J. van Heijenoort, 1980, *Biosynthesis of the peptidoglycan of Escherichia coli K-12: properties of the in vitro polymerization by transglycosylation,* FEBS Lett. 110(2): 241–4.

This approach has significant limitations: 1) the amount of lipid II in bacterial cells is small, approximately 2000 molecules per cell (see, e.g., van Heijenoort, Y., M. Gomez, M. Derrien, J. Ayala, and J. van Heijenoort, 1992, *Membrane intermediates in the peptidoglycan metabolism of Escherichia coli: possible roles of PBP 1b and PBP 3.* J Bacteriol. 174(11):3549–57 [published erratum appears in J Bacteriol. 1992 September;174(18):6004]); 2) purification is a lengthy process, with significant loss of material occurring during purification (see, e.g., van Heijenoort, supra and references cited therein); 3) little is known about the structure of purified lipid II and its ability to be used efficiently as a substrate (see, e.g., van Heijenoort, supra; Matsuhashi supra); 4) the lipid II has to be reintroduced into bacterial membranes in order to be a substrate for a transglycosylase; and 5) only a fraction of the lipid II substrate is enzymatically converted to peptidoglycan product. All of these limitations impair the ability to monitor polymerization of lipid II into peptidoglycan by the action of a transglycosylase enzyme, therefore, the use of purified lipid II as a substrate to perform the large number of transglycosylase assays required for identifying inhibitors in chemical or natural product inventories is neither practical nor feasible. In addition, this assay format limits the ability to further characterize the known natural product inhibitors such as moenomycin and analogs thereof, as well as any newly identified inhibitors of transglycosylase function. See, e.g., El-Abadla, N., M. Lampilis, L. Hennig, M. Findeisen, P. Welzel, D. Muller, A. Markus, and J. van Heijenoort, 1999, *Meonomycin A: The role of the methyl group in the moenuronamide unit and a general discussion of structure-activity relationships,* Tetrahedron, 55:699–722; M. Ge, Z. Chen, H. R. Onishi, J. Kohler, L. L. Silver, R. Kerns, S. Fukuzawa, C. Thompson and D. Kahne, (1999), *Vancomycin derivatives that inhibit peptidoglycan biosynthesis without binding D-Ala-D-Ala,* Science. 284:507–11.

The most recent attempt to improve on the ability to conduct transglycosylase assays relied on modifications of the methods used in preparation and purification, but only improved the yield of lipid II substrate from 2% to 18%. van Heijenoort, Y., M. Gomez, M. Derrien, J. Ayala, and J. van Heijenoort, 1992, *Membrane intermediates in the peptidoglycan metabolism of Escherichia coli: possible roles of PBP 1b and PBP 3,* J Bacteriol. 174(11):3549–57 [published erratum appears in J Bacteriol 1992 September;174(18): 6004].

Some antibiotics, such as vancomycin, inhibit peptidoglycan synthesis by binding to cell wall intermediates that contain a dipeptide D-ala-D-ala moiety. A. Malabarba, T. I. Nicas and R. C. Thompson, (1997), *Structural modifications of glycopeptide antibiotics,* Med Res Rev. 17, 69–137; R. Nagarajan, (1993), *Structure-activity relationships of vancomycin-type glycopeptide antibiotics,* J Antibiot (Tokyo), 46, 1181–95. Unfortunately, the increased clinical use of vancomycin has selected for vancomycin resistant *Enterococci,* which replace the final D-ala of the dipeptide with a lactate moiety (D-lac), such that D-ala-D-ala is replaced with D-ala-D-lac, leading to a 1000-fold decrease in drug:ligand interaction and MIC. C. T. Walsh, S. L. Fisher, I. S. Park, M. Prahalad and Z. Wu, (1996), *Bacterial resistance to vancomycin: five genes and one missing hydrogen bond tell the story,* Chem Biol. 3, 21–8; C. T. Walsh, (1993), *Vancomycin resistance: decoding the molecular logic,* Science. 261, 308–9 [published erratum appears in Science Oct. 8, 1993; 262(5131):164]; R. Leclercq and P. Courvalin, (1997), *Resistance to glycopeptides in enterococci,* Clin Infect Dis. 24, 545–54; R. Leclercq, (1999), *Glycopeptides: mechanism ofaction and of resistance,* Presse Med., 28, 720–1; M. Arthur, P. E. Reynolds, F. Depardieu, S. Evers, S. Dutka-Malen, R. Quintiliani, Jr. and P. Courvalin, (1996), *Mechanisms of glycopeptide resistance in enterococci,* J Infect. 32, 11–6. However, certain natural product and semi-synthetic glycopeptide analogs are known which have potent activity against vancomycin resistant *Enterococci.* See, e.g., Malabarba, supra; M. Ge, Z. Chen, H. R. Onishi, J. Kohler, L. L. Silver, R. Kems, S. Fukuzawa, C. Thompson and D. Kahne, (1999), *Vancomycin derivatives that inhibit peptidoglycan biosynthesis without binding D-Ala-D-Ala,* Science. 284, 507–11. These include teicoplanin, eremomycin, chloroeremomycin, and novel vancomycin analogs.

The antibacterial activity of such novel compounds against bacteria that lack the D-ala-D-ala binding site was explained based on two fundamentally different hypotheses. The first evokes a combination of membrane anchoring and drug dimerization for specific glycopeptide analogs that leads to enhancement of the weak interaction with D-ala-D-lac. D. H. Williams, (1996), *The glycopeptide story—how to kill the deadly 'superbugs',* Nat. Prod. Rep. 13, 469–77; N. E. Allen, D. L. LeTourneau and J. N. Hobbs, Jr., (1997), *Molecular interactions of a semisynthetic glycopeptide antibiotic with D-alanyl-D-alanine and D-alanyl-D-lactate residues,* Antimicrob. Agents Chemother., 41, 66–71.

The second proposes inhibition of the transglycosylases responsible for polymerization of intermediates into peptidoglycan. Ge et al., supra. Until the present invention, there was no straightforward method available for determining which of these hypotheses was correct for particular inhibitors. The present invention's transglycosylase assay provides a method of determining which of these hypotheses is correct, using the UDP-MurNAc-tetrapeptide substrate, which lacks the D-ala-D-ala dipeptide.

Additionally, until the present invention, there was no simple, reproducible assay for monitoring the enzymatic activity of bacterial transglycosylase. Thus the ability to discover and validate inhibitors of transglycosylase function by assaying large numbers of compounds in chemical or natural product inventories was not feasible. In addition, it was difficult to further characterize the known natural product inhibitors of transglycosylase activity, such as moenomycin, or any other putative transglycosylase inhibitors.

Co-owned U.S. Provisional Patent Application No. 60/097,324, filed Aug. 20, 1998, discloses an assay employing a biotinylated MurNAc-pp substrate, which biotin moiety allows for the capture, separation, and measurement of lipid II and peptidoglycan, and the subsequent testing of potentially inhibitory compounds. However, the disclosed method is still unable to assess which step in the biosynthetic pathway is being inhibited.

U.S. Provisional Patent Application Ser. No. 09/241,862 discloses synthetic analogs of lipid I for use in assays measuring transglycosylase activity, however, the disclosed assays require the synthesis of such analogs. Moreover, the analogs have not been shown to yield lipid II substrate which is active in the transglycosylation step of the peptidoglycan synthesis pathway.

U.S. Provisional Patent Application No. 60/122,966 discloses synthetic analogs of lipid II for use in assays directly measuring transglycosylase activity, however, the disclosed assays require the synthesis of such analogs. Moreover, the analogs have not been shown to act as substrate for the transglycosylation step of the peptidoglycan synthesis pathway.

The art is in need of assay methods for directly measuring transglycosylase activity without the need for cumbersome purification of substrate, or production of synthetic analogs, in order to assess potential inhibitors, identify which stages of the biosynthetic pathway are being inhibited, and ascertain the likelihood that such identified inhibitors would be effective against otherwise resistant bacteria.

SUMMARY OF THE INVENTION

The present invention provides a simplified assay method for directly measuring transglycosylase activity, as well as methods to validate activity of, and further characterize, putative inhibitors. The assay utilizes conditions wherein the substrate, N-acetylglucosamine-β-1,4-MurNAc-pentapeptide-pyrophosphoryl-undecaprenol (lipid II), is generated in labeled form in situ, and subsequently used without the need for purification as a substrate for either native, heterologously expressed, or purified transglycosylase. The biosynthetic pathway is halted in situ following the formation of lipid II, and is allowed to proceed to peptidoglycan formation only when sufficient lipid II quantities have been reached. The blocking of the peptidoglycan formation stage allows lipid II to accumulate, hence there is no need to purify the lipid II substrate.

Bacteria are grown to sufficient number to provide sufficient intact membranes for use in the assay. Bacteria are permeabilized by any technique, many of which are known in the art, for example, but not limited to, freezing and thawing, ether-permeabilizing, and French pressing. UDP-MurNAc-peptide and labeled UDP-GlcNAc are mixed with the isolated membranes. MurNAc is incorporated into lipid I by the MraY enzyme. The labeled GlcNAc is incorporated into lipid II in the reaction catalyzed by the enzyme MurG. The addition of a transglycosylation blocker, such as, for example, a detergent (e.g., 0. 1% Triton X-100®) in the reaction mixture prevents and blocks the transglycosylation of lipid II into peptidoglycan, thereby causing the accumulation of lipid II in the reaction mixture. Removal of the transglycosylation blocker (e.g., the detergent) allows the transglycosylation of lipid II to proceed, generating labeled peptidoglycan. The peptidoglycan product may then be detected either by separating substrate from product (e.g., via acid precipitation), followed by measurement of the amount of product formed, or by direct measurement of product formation without removal of substrate. The assay is compatible with various forms of measurement of product formation using any of a variety of labels, e.g., radioactivity, fluorescent or other optical techniques, specific labeled antibodies that recognize product, etc.), and combinations of these labels, and the assay is amenable to microtiter and solid phase formats.

Instead of bacterial membranes, the assay of the invention may also be performed with purified substrates, synthetic analogs thereof, and purified enzymes. As with the membrane-based assay, a transglycosylation blocker is used to halt the peptidoglycan synthesis pathway at the lipid II stage, and then removed to allow peptidoglycan formation.

In order to assess the efficacy of a putative inhibitor of peptidoglycan formation, which may inhibit any step of the transglycosylation pathway from the formation of lipid I through the formation of lipid II and the ultimate polymerization mediated by transglycosylase, the inhibitor may be added to the reaction mixture without the presence of detergent Lack of peptidoglycan would thus confirm an inhibitory effect. However, one of skill in the art would still be unable to determine whether the inhibitory effect was being asserted at the transglycosylase-mediated transglycosylation stage, or at an earlier stage in the pathway.

In order to determine which stage the inhibitor is affecting, the inhibitor may be added to the reaction mixture while a transglycosylation blocker is present. Accumulation of labeled lipid II may then be measured. If lipid II does not accumulate in the presence of the inhibitor, then the inhibitor must be exerting its effect at either the lipid I or lipid II production stage. If lipid II does accumulate, the detergent may be removed, thereby allowing the transglycosylation step to proceed. Labeled peptidoglycan may then be measured. Lack of peptidoglycan synthesis would thus confirm the action of the inhibitor as exerting an inhibitory effect at the transglycosylase-mediated transglycosylation stage.

Some antibiotics may inhibit not only the formation of lipid II, but may also directly inhibit transglycosylase-mediated peptidoglycan formation. The method of the invention is capable of characterizing such an antibiotic inhibitor. In the reaction described above, lipid II would fail to accumulate. However, by simply introducing the inhibitor after the lipid II has accumulated (i.e., all the $^{14}C$ labeled UDP-GlcNAc precursor has been incorporated into lipid II), and then removing the transglycosylase blocker (e.g., a detergent), transglycosylase activity would resume unless the putative inhibitor also inhibits such activity. A lack of peptidoglycan synthesis confirms such inhibitory activity.

A second assay using UDP-MurNAc-pentapeptide or UDP-MurNAc-tetrapeptide substrates and appropriate enzyme systems allows one to validate inhibition at the transglycosylase-mediated transglycosylation stage in a substrate independent manner. UDP-MurNAc-tetrapeptide lacks the identified D-ala-D-ala binding site for many inhibitors. Thus, the tetrapeptide precursor may be used to distinguish inhibitors by whether they rely upon the presence of that binding site. The first step of the assay allows for the preferential synthesis and accumulation of lipid II by reaction mixtures containing French pressed cell wall membranes, exogenously supplied UDP-MurNAc pentapeptide or tetrapeptide, and radiolabeled UDP-GlcNAc. The UDP-MurNAc-peptide is required for the synthesis of lipid I, and UDP-GlcNAc allows for the subsequent synthesis and labeling of lipid II. When incubated in the presence of a transglycosylation blocker, e.g., 0.1% Triton X-100®, the product is almost exclusively lipid II, while the subsequent formation of peptidoglycan is inhibited. The removal of the transglycosylation blocker (in this case Triton X-100®) results in the synthesis of peptidoglycan from the accumulated lipid II. This reaction is sensitive to the known transglycosylase inhibitor moenomycin. In addition, tunicamycin, which affects an earlier step of the pathway by inhibiting MraY (and thus lipid I formation), had no effect on the formation of peptidoglycan in this assay. The ability to differentiate inhibition of transglycosylase activity from inhibition of earlier steps in the pathway has led to the discovery that the antibiotic vancomycin, which binds the D-ala-D-ala dipeptide moiety on lipid II and thus inhibits the formation of peptidoglycan, also is capable of inhibiting the formation of lipid II in vitro. The assay has been used to confirm that a number of novel compounds synthesized at Incara Research Labs (IRL) specifically inhibit the transglycosylation stage.

Using the methods of this invention, at least two vancomycin derivatives, chlorobiphenyl-vancomycin (CBP-V) and chlorobiphenyl-desleucyl-vancomycin (CBP-dl-V), have been identified which have been confirmed as directly inhibiting the transglycosylase-mediated transglycosylasation reaction.

The ability to identify the mode of action of an inhibitor, that is, the stage in the pathway where its effects are exerted, is an important contribution of the present invention. This ability allows one of skill in the art to evaluate inhibitors for characteristics such as specificity (i.e., general or particular), as well as the likelihood of side effects, and other characteristics.

DETAILED DESCRIPTION OF THE INVENTION

Definitions

All terms herein have their commonly understood meanings as used in the art, however, the following terms are specifically defined:

Substance: A matter of particular or definite chemical constitution. As disclosed herein, a substance can include small molecules, peptides, proteins, carbohydrates, nucleic acids and combinations, derivatives, homologs and analogs thereof An analog of a particular substance includes a modified form of the substance, such as the addition, removal, or substitution of particular consituents of the initial substance. In the present invention, an analog is frequently referred to in the context of a modied UMP, Lipid I, Lipid II, or peptidoglycan.

Label: A "label" or "labeled" substance means that an original substance is modified to include or incorporate a label such that the label permits the detection, capture, or otherwise, monitoring of the labeled substance, which labeled substance may have undergone or participated in a chemical transformation, particularly, but not limited to, those transformations that are mediated by bacterial cell wall biosynthesis enzymes of potential interest. A "label" is also useful for distinguishing a compound by introducing thereto a traceable constituent. The label can take many forms, including but not limited to conventional radioisotopic labeling; chemical labeling, including metals, chelators, peptides, nucleic acids, receptors, lectins; immunogenic labeling, or a label with light scattering effect, and the like. Suitable methods to detect such labels are scintillation counting, autoradiography, fluorescence measurement, calorimetric measurement, or light emission measurement. In certain embodiments of the invention, a label may include a capture moiety, as defined further below.

Thus, the labeling may comprise a radiolabel (e.g. $^{14}$C, $^{32}$P, $^{3}$H, and the like), an enzyme (e.g., peroxidase, alkaline or acid phosphatase, and the like), a bacterial label, a fluorescent label, an antibody (which may be used in a double antibody system), an antigen (to be used with a labeled antibody), a small molecule such as biotin (to be used with an avidin, streptavidin, or antibiotin system), a latex particle (to be used in a buoyancy or latex agglutination system), an electron dense compound such as ferritin (to be used with electron microscopy), or a light scattering particle such as colloidal gold, or any combinations or permutations of the foregoing.

For example, if the labeling portion of a substrate probe is an antigen, a signal can be generated by complexing the antigen with an antibody/enzyme conjugate, followed by addition of an enzyme substrate. If this portion were an antibody, signal can be generated by complexing antiantibody or an FC binding protein such as Protein A therewith, when such second antibody or Protein A have been conjugated to an enzyme.

For reasons of ease and safety in the handling of the assay, it is preferred that it be chemically labeled, especially enzymatically or immunologically. In more preferred embodiments, the chemical label of choice is a hapten such as biotin, iminobiotin, fluorescein and the like.

Among the preferred labeling systems are those based on the biotin/strepavidin system. This system can be incorporated into the substrate by a variety of means. For example, the probe can be covalently attached to biotin via a cytochrome C bridge (see, Manning et al., in Biochemistry (1977) 16:1364–1370; Manning et al, in Chromosoma (1975) 53:107–117; Sodja, A., in Nucleic Acids Research (1978) 5:385–401)), or it can be covalently incorporated into specific nucleotide residues (see, Langer, P. R., PNAS, USA (1981) 78:6633–6637), or the biotin can be attached to a polynucleotide by means of a diamine (e.g., pentane diamine) bridge (Broker, T. R., et al, in Nucleic Acids Research (1978) 5:363–384). Interaction of the biotin molecules with avidin, streptavidin or antibiotin antibodies is then carried out, wherein the avidin, streptavidin or the other moiety of interst is conjugated to such signaling components as latex particles (see, Sodja, A., et al, supra, or Manning, et.al., in Chromosoma, supra) or ferritin (see, Broker, supra) a fluorogen such as fluorescein, an enzyme, secondary antibodies, magnetic particles, or the like.

Peptidoglycan: A chemical composition which is part of the cell wall and consists of repeating subunits of crosslinked N-Acetyl glucosamine and N-acetylmuramic acid.

Capture Agent: A substance, generally bound to a solid substrate,which is capable of capturing and separating another substance that is labeled, or more specifically, which bears a capture moiety, from a mixture comprising the substance bearing the label or capture moiety. The capture could be biochemical or mechanical in nature, or a combination thereof. An example of a capture agent is avidin or streptavidin bound directly or indirectly (e.g., via a linker molecule) to the surface groups of glass, nicroparticles, plastic beads, gel beads, or the like.

Transglycosylation Blocker: A blocker of transglycosylation activity. Any agent may be used that differentially blocks the transglycosylase stage (as opposed to the reactions mediated by MraY and MurG) in a reversible manner. These may include detergents, covalent adducts to essential sulfhydryl groups, other antibiotics, temperature (e.g., the use of membranes from genetically engineered bacteria containing temperature sensitive enzymes). Any reaction condition that preferentially prevents the formation of peptidoglycan while allowing for the formation of lipid II and is reversible may be used in the methods of the invention.

Detergent: Any agent that is capable of emulsifying oil, and/or which acts as a wetting agent or surfactant. Examples of useful detergents include but are not limited to: nonionic detergents, cationic detergents, anionic detergents, branched polyoxyethylene ethers (e.g., Triton®), polyoxyethylene isooctylphenyl ether (e.g., polyoxyethylene (10) isooctylphenyl (e.g., Triton X-100®, Sigma Chemical, St. Louis, Mo.)), Tween 20, APO-10, APO-12, Big CHAP, Big CHAP, Deoxy, BRIJ7 35, PROTEIN GRADE7 Detergent, 10% Solution, C10E6, C10E8, C12E6, C12E8, C12E9, Cyclohexyl-n-ethyl-β-D-maltoside, Cyclohexyl-n-hexyl-β-D-maltoside, Cyclohexyl-n-methyl-β-D-maltoside, n-Decanoylsucrose, n-Decyl-β-D-glucopyranoside, n-Decyl-β-D-maltoside, n-Decyl-β-D-thiomaltoside, Digitonln, Digitonln (High Purity), n-Dodecanaylsucrose, n-Dodecyl-βD-glucopyranoside, n-Dodecyl-β-D-maltoside, ELUGENTJ Detergent, GENAPOL7 C-100, PROTEIN GRADE7 Detergent GENAPOL7 X-80, PROTEIN GRADE7 Detergent, GENAPOL7 X-100®, PROTEIN GRADE7 HECAMEG, n-Heptyl-β-D-glucopyranoside, n-Heptyl-β-D-thioglucopyranoside, 10% Solution, n-Hexyl-β-D-glucopyranoside, MEGA-8, MEGA-9, MEGA 10, n-Nonyl-β-D-glucopyranoside, NP-10, NP-40, PROTEIN GRADE7 Detergent, n-Octanoyl-β-D-glucosylamine (NOGA), n-Octanoylsucrose, n-Octyl-β-D-glucopyranoside, n-Octyl-β-D-glucopyranoside, n-Octyl-β-D-maltopyranosiden-Octyl-β-D-thioglycopyranoside, PLURONIC7 F-68, PLURONIC7 F-127, PROTEIN GRADE7, n-Undecyl-β-D-maltoside and the like. These and other detergents are easily available to those in the art from standard chemical supply houses (e.g., Sigma Chemical, St. Louis, Mo.). The detergents may also comprise other compounds, for example, polyethylene glycol.

Preferred Embodiments

The present invention solves the problems related to preparation, purification, and reintroduction of lipid II into membranes for use as substrate for transglycosylases, by utilizing endogenous synthesis of lipid II by bacteria, and its controlled use as a substrate for transglycosylase in situ. There is no need to purify lipid II, and no problems associated with reintroduction of lipid II into the membrane for use by transglycosylase. Methods were invented that allow the synthesis of endogenous lipid II using reagents that can contain specific labels for tagging lipid II ($^{14}$C-glucosamine introduced from UDP-N-acetyl-glucosamine, a biotin tag from UDP-MurNAc-pentapeptide labeled with biotin on the epsilon amino group of lysine, or other groups such as fluorescent reporters e.g. dansyl etc.), under conditions where lipid II is not used as a substrate for transglycosylases due to the presence of an a transglycosylation blocker. Thus, labeled lipid II is synthesized and accumulated in the bacterial membrane. Additional methods are provided whereby the effects of the transglycosylation blocker could be effectively removed, thereby allowing labeled lipid II to be used as substrate for transglycosylase, and thus be polymerized into peptidoglycan. Measuring the conversion of labeled lipid II into peptidoglycan then monitors the polymerization of lipid II into peptidoglycan by the action of transglycosylase by one of several possible methods. This novel assay allows the reproducible measurement of transglycosylase activity in microtiter mode, and increases the number of reactions that can be performed to a rate compatible with discovering inhibitors in compound inventories. Such inhibitors could act by inhibiting transglycosylase directly, or indirectly by binding to the lipid II substrate, or by inhibiting any other reaction mechanism required to perform the transglycosylation process. The assay design will also aid in follow up of the activity of other compounds, as was accomplished for moenomycin and several vancomycin analogs.

Generally, in a preferred embodiment of the invention, the assay of the invention is performed as follows: An initial mixture is prepared with a buffer comprising 50 mM Tris (pH=8.0), 42 mM MgAc, 208 mM KCl, to which is added a transglycosylation blocker, e.g., 0.1% Triton X-100®, if desired for blocking transglycosylase activity. The reaction may be performed in ways amenable to microtiter plates, for example, in a 50μl reaction volume, which may contain 25 μg French Pressed bacterial membranes. The precursors which may be present are UDP-MurNAc-peptide and UDP-GlcNAc, and are present in sufficient quantities to yield sufficient lipid I and lipid II upon reaction with the involved enzymes, for example, 0.5 nmoles UDP-MurNAc-pentapeptide 10% DMSO final concentration (which generally is added in conjunction with a putative inhibitor), and 0.5 μM GlcNAc. In one embodiment, the UDP-GlcNAc is labeled, such as with $^{14}$C such that the $^{14}$C labeled UDP-GlcNAc is present in the reaction mixture at about 20,000 CPM. In another embodiment, the UDP-MurNAc-peptide is also labeled, such as with biotin.

All components except $^{14}$C labeled UDP-GlcNAc are pre-incubated together for 10 minutes at room temperature. The reaction mixture is incubated an additional about 15 minutes to about 2 hours, preferably about 1 hour, after addition of the labeled UDP-GlcNAc. Paper chromatography analysis demonstrates that these assay conditions yield no peptidoglycan while incorporating all the labeled GlcNAc into lipid II. The removal of the transglycosylation blocker Triton X-100® from the buffer allows for the formation of peptidoglycan over an incubation period of about 30 minutes to about 2 hours, preferably about 2 hours.

The assay described above can be further modified to facilitate performance of the variations of the assays of the invention, and to simplify detection of peptidoglycan product. The transglycosylation blocker may be any agent that differentially blocks the transglycosylase stage (as opposed to the reactions mediated by MraY and MurG) in a reversible manner.

In a preferred embodiment, the transglycosylation blocker is a detergent, more preferably the detergent Triton X-100®. It is preferred to use Triton X-100® in a range from about 0.02% to about 0.5%, more preferably from about 0.075% to about 0.25%, and more preferably about 0.1%. For other transglycosylation blockers, the amount useful in the present invention will be readily apparent to one skilled in the art, once armed with the present disclosure. Generally, amounts used are in lower ranges (i.e., about 0.05%), and, if necessary, increased until the desired blocking effect is achieved.

Depending on the nature of the transglycosylation blocker, its "removal" indicates any means of nullifying its effect, and may take the form of actual elimination, dilution, binding, destruction, filtration, or the like.

The general form of the assay described above is ideally suited for distinguishing between putative inhibitors which directly inhibit transglycosylase-mediated transglycosylation and those which exert their inhibitory effects at an earlier stage of the pathway. The presence of the transglycosylation blocker permits the accumulation of lipid II, which will only accumulate if the inhibitor does not inhibit lipid I or lipid II formation. Lipid II will not accumulate if the inhibitor inhibits an earlier stage.

In an embodiment of the invention better suited to characterizing inhibitors that inhibit lipid II formation as well as directly inhibiting transglycosylase-mediated transglycosylation, the inhibitor is not added to the reaction mixture (which contains transglycosylation blocker) until after the two reactions have occurred, thereby allowing for the accumulation of lipid II (there being no inhibitor present at that time). The inhibitor is then added, and the transglycosylation blocker is removed, thereby allowing peptidoglycan formation to proceed. An inhibitor that inhibits only at an early stage will have no effect on peptidoglycan formation in this embodiment of the assay, while an inhibitor that does directly inhibit transglycosylase will show its inhibitory effects. Using this embodiment of the invention, one can identify inhibitors that block early stages and directly inhibit transglycosylase-mediated transglycosylation, such as vancomycin. It has been shown that vancomycin is able to bind to the D-ala-D-ala dipeptide of lipid II, thereby directly inhibiting the ability of a transglycosylase enzyme to mediate the peptidoglycan synthesis reaction. Vancomycin is unable to cross the cell membrane of intact cells. However, when performing the assay of the invention in vitro, vancomycin is also able to bind to the D-ala-D-ala dipeptide present on the MurNAc-pentapeptide moiety of lipid I, thereby inhibiting the formation of lipid II. Thus vancomycin can be said to inhibit both the earlier stage of lipid II formation, as well as the transglycosylase-mediated step, although in vivo it would only inhibit the action of the transglycosylase enzyme (via binding to the dipeptide of lipid II).

In another embodiment, UDP-MurNAc-pentapeptide and UDP-MurNAc-tetrapeptide are purified from bacteria and used to evaluate the inhibitory potency of select compounds in in vitro peptidoglycan synthesis. Compounds that act as inhibitors of transglycosylation would be expected to be equipotent at inhibiting peptidoglycan synthesis using either precursor substrate, since only an inhibitor that binds to the D-ala-D-ala dipeptide would demonstrate differential potency between the two. The system is validated by showing the equipotent inhibition caused by moenomycin, a known direct inhibitor of transglycosylase, and was used to validate inhibition of the transglycosylase- mediated transglycosylation process by synthetic disaccharide analogs of moenomycin. Using this method, several synthetic analogs of vancomycin synthesized by Intercardia Research Labs were shown to specifically inhibit transglycosylation.

As reported by Allen, N. E., D. L. LeTourneau, and J. N. Hobbs, Jr., 1997, *Molecular interactions of a semisynthetic glycopeptide antibiotic with D-alanyl-D-alanine and D-alanyl-D-lactate residues,* Antimicrob Agents Chemother. 41(1):66–71, an assay was used in an attempt to characterize the mode of action of a specific glycopeptide analog (LY191145). Those authors concluded that LY191145 inhibited the transglycosylation step in a substrate dependent manner requiring a direct interaction with the terminal D-ala-D-ala or D-ala-D-lac residues in peptidoglycan precursors (e.g., MurNAc, lipid I, or lipid II). Those authors used the Gram-positive bacterium *Aerococcus viridens* as a source of membranes to monitor peptidoglycan synthesis using UDP-MurNAc-pentapeptide and UDP-MurNAc-tetrapeptide. They selected moenomycin as the best known representative of a compound that inhibits "membrane-associated reactions in peptidoglycan synthesis by D-ala-D-ala independent mechanisms". Their results show very poor inhibition by moenomycin (<35% at 100 $\mu$g/ml). This result is expected based on the present inventors' studies, which show that moenomycin does not effectively inhibit peptidoglycan synthesis in all Gram-positive bacteria. Thus the ability of compounds to inhibit the transglycosylation stage depends, to some extent, on the bacterial strain used in testing. The conclusions reached by Allen et al. may relate to the choice of Gram-positive organism used. Indeed, the present inventors' studies show that related glycopeptide structures with similar antibacterial activities to LY191145 do inhibit peptidoglycan synthesis when either UDP-MurNAc-pentapeptide or UDP-MurNAc-tetrapeptide is used as substrate, and the source of enzymes is the Gram-negative bacterium *E. coli.* Thus use of the *E. coli* as the source of synthetic enzymes does allow one to validate that compounds act by inhibition of "membrane-associated reactions in peptidoglycan synthesis by D-ala-D-ala independent mechanisms". Moenomycin is a particularly effective inhibitor of the *E. coli* system using either UDP-MurNAc-pentapeptide or UDP-MurNAc-tetrapeptide, with potencies that are 4 orders of magnitude greater than those measured in Allen et al. using *A. viridens.*

One of skill in the art may also further characterize an inhibitor which affects an early stage as well as directly inhibiting transglycosylase-mediated transglycosylation using another embodiment of the present invention in which the UDP-MurNAc-peptide precursor is present in a tetrapeptide form and a pentapeptide form in separate samples. This permits analysis of putative inhibitors which are suspected of binding to the D-ala-D-ala dipeptide moiety. If such an inhibitor does bind to the dipeptide, the presence of MurNAc-tetrapeptide as the precursor prevents such binding, allowing formation of lipid II to proceed, while the presence of MurNAc-pentapeptide allows such binding, preventing formation of lipid II.

In additional embodiments, use of UDP-MurNAc-peptides containing fluorescent adducts, or fluorescent and fluorescent-quenching adducts, allows detection of peptidoglycan product via optical measurements.

In yet another embodiment, incorporation of an adduct like biotin of dinitrophenyl into the peptide allows detection with the use of an antibody or another affinity probe.

In another embodiment, in order to extend the assay's usefulness to measurement of specific transglycosylase activities, cells or membranes from other bacteria could be used. In addition, heterologous expression of specific transglycosylases from other organisms allows for assays of selected transglycosylase activities. For example, heterologous expression of active PBP1A from *Haemophilus influenzae* (Sharma, U. K., P. Dwarakanath, N. Banerjee, C. Town, and T. S. Balganesh, 1995, *Expression and characterization of the ponA (ORF I) gene of Haemophilus influenzae: functional complementation in a heterologous system,* J Bacteriol. 177(23):6745–50) and PBP1B from *Citrobacter freundii* (Di Berardino et al., supra) has been shown in *E. coli* containing a defect in PBP1B. Use of the current invention's methods allows measurement of the transglycosylase activity of these enzymes.

In another embodiment, one may use genetic fusion of transglycosylase domains from other organisms to specific elements of *E. coli* PBP genes to create functional hybrid proteins as was reported by Zijderveld, C. A., Q. Waisfilsz, M. E. Aarsman, and N. Nanninga, 1995, *Hybrid proteins of the transglycosylase and the transpeptidase domains of PBP1B and PBP3 of Escherichia coli*, J Bacteriol. 177(21): 6290–3. Expression of such hybrids in *E. coli* lacking PBP1B, coupled with use of the invention, allows measurement of the transglycosylase activity of transglycosylase domains cloned from selected organisms. Another embodiment includes adding exogenous transglycosylase purified from selected bacteria to the described in vitro system, thus allowing measurement of transglycosylase activity in purified proteins.

The methods of the invention as described employ membranes isolated from *E. coli* as the source of enzymes both for the formation of lipid II, and for the subsequent formation of peptidoglycan. This validates the transglycosylase step as a potential target for inhibition based on the effect seen with moenomycin in this assay, and correlates with the in vivo effects with permeability mutants of *E. coli*. However, one may also construct gene knockout mutations of key transglycosylases in the *E. coli* background and introduce heterologous transglycosylase genes from clinically relevant Gram positive organisms such as *Enterococcus*, *Staphylococcus*, and *Streptococcus*. A similar approach would be to develop assay conditions using membranes isolated from Gram positive organisms as a source of endogenous transglycosylases along with the accompanying cell wall machinery.

The methods of the present invention have tremendous potential for screening large numbers of compounds for inhibitors of the transglycosylase step. The reactions are amenable to microplate formatting, with separation being routinely performed by differential extractions, or precipitation and subsequent filtering in microtiter plates. Routine labeling of the UDP-MurNAc-peptides used as substrates may be performed with biotin, which allows for both a convenient method for purification as well as direct measurement of products which contain both biotin and radiolabel.

Another embodiment of the invention is an assay kit comprising labeled and/or unlabeled MurNAc, labeled GlcNAc, a transglycosylation blocker, and instructions.

The methods of the invention are useful for assaying other enzymes that use lipid-linker intermediates in the synthesis of cellular products, and for which a reversible enzyme blocker may be employed. Bacterial capsules and O-antigen are also synthesized using the same lipid (undecaprenol) used in peptidoglycan synthesis. A related lipid (dolichol) is used to carry intermediates used in the synthesis of various carbohydrate material present in eucaryotic cells (e.g. mannan in yeast and fungi, and glycoproteins in eucaryotic cells).

EXAMPLES

The present invention is further illustrated by way of the following Examples which are intended to elucidate the invention. These Examples are not intended, nor are they to be construed, as limiting the scope of the invention. It will be clear to those of skill in the art that the invention may be practiced otherwise than as particularly described herein. Numerous modifications and variations of the present invention are possible in view of the teachings herein and, therefore, are within the scope of the invention.

Example 1

Accumulation of Lipid II Using Triton X-100®

Assay conditions used for the formation of lipid II were exploited to preferentially prevent the formation of peptidoglycan from lipid intermediates, but still allow the formation and accumulation of lipid II in situ. For this Example, and those that follow, Triton X-100® was used, which demonstrated inhibition of the formation of peptidoglycan when used at 0.1% concentration, while not affecting the formation of lipid II. Previous experimental data had shown that 0.01% Triton X-100® did not inhibit peptidoglycan formation. As described above, however, any reversible transglycosylation blocker may be used.

Reactions were performed in the following buffer: 50 mM Tris (pH=8.0), 42 mM MgAc, 208 mM KCl, and 0.1% Triton X-100®. Each reaction was performed in a 50 ul reaction volume, containing 25 µg French Pressed bacterial membranes, 0.5 nmoles biotinylated UDP-MurNAc-pentapeptide 10% DMSO final concentration (added in conjunction with inhibitor), and 0.5 uM 14C-GlcNAc (≈20, 000 CPM). All components except 14C-GlcNAc were pre-incubated together for 10 min at room temperature. The reactions were incubated an additional 1 hour after addition of $^{14}$C-GlcNAc. The removal of Triton X-100® from the buffer allowed for the formation of peptidoglycan.

Paper chromatography analysis demonstrated that the assay conditions being employed produce no peptidoglycan while converting all the $^{14}$C-GlcNAc to lipid II.

Initial experiments performed by diluting the reaction mixtures to reduce the Triton X-100® concentration to 0.01% demonstrated that it was possible to reverse the inhibition of peptidoglycan formation. To make the reaction volume more manageable, the Triton was removed with the addition of Detergent-Out resin (Geno-Technology, St. Louis, Mo.). After binding up the inhibiting detergent, the reaction was further incubated for 2 hours to allow for transglycosylation to proceed. The amount of peptidoglycan formed by this manipulation was equivalent to that produced in reaction mixtures containing no Triton X-100® from the beginning.

Example 2

Comparison Using Moenomycin With and Without Blocker

The present inventors developed a method for using the endogenous production of lipid II for the specific purpose of identifying inhibitors of the transglycosylation step. The sensitivity of the assay to moenomycin was tested and compared to peptidoglycan inhibition in assays where no transglycosylation blocker was used. Moenomycin, a known inhibitor of the transglycosylase-mediated transglycosylation reaction, had identical IC50 values between the two sets of data, confirming that the assay of the invention may be used to identify those compounds that have as yet an unknown ability to inhibit the transglycosylation step. Thus, the addition and subsequent removal of a transglycosylation blocker does not impair the ultimate total production of peptidoglycan; it simply arrests the pathway at a stage convenient for scientific analysis.

Example 3

Identification of Inhibitors of Transglycosylation

Figure 2:
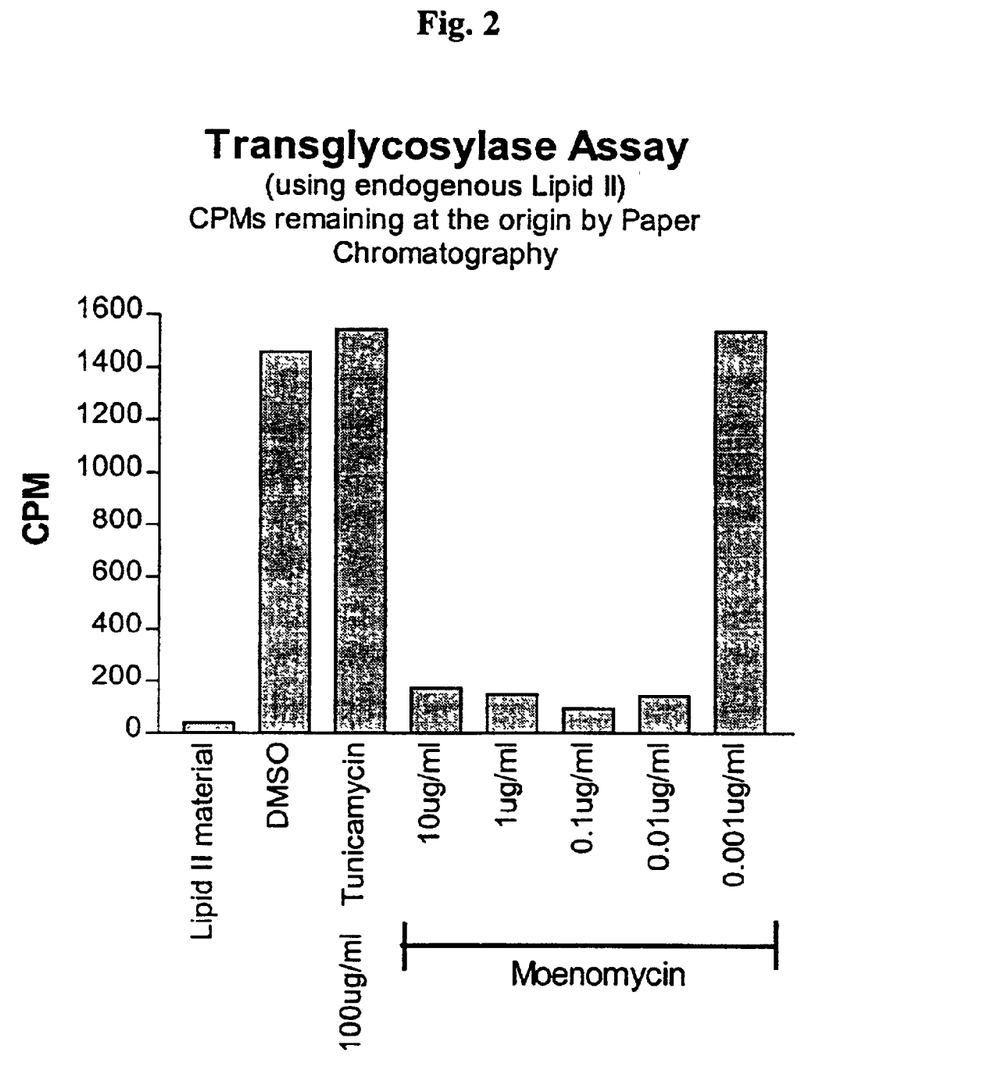
FIG. 2 is a graph showing the results of the method of the invention using the inhibitors tunicamycin and moenomycin, and using MurNAc-pentapeptide.
Figure 3:
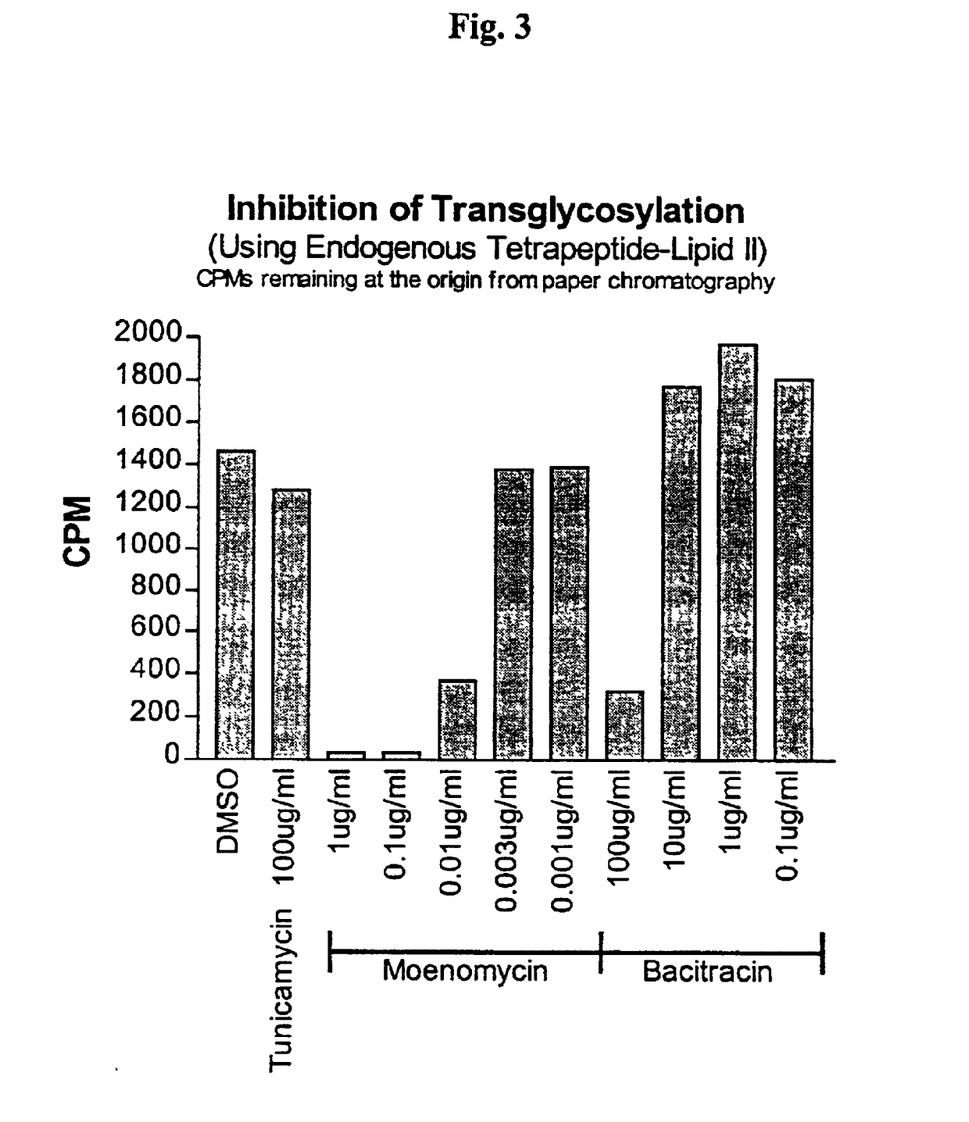
FIG. 3 is a graph showing the results of the method of the invention using the inhibitors tunicamycin and moenomycin, and using MurNAc-tetrapeptide.

The above-described methods of the invention were used to analyze the activity of three inhibitors. The assay included separate samples of tunicamycin, moenomycin, or bacitracin in various concentrations. These inhibitors were added to their respective samples after formation of lipid II, with the subsequent removal of the transglycosylation blocker Triton X-100®. After 2 hours incubation, aliquots of the solubilized products were analyzed by ascending paper chromatography. The amount of lipid II converted into peptidoglycan is represented by the amount of radioactivity measured in CPM remaining at the origin for each reaction. Tunicamycin had no measurable effect on peptidoglycan production, which was to be expected because tunicamycin is known to inhibit MraY, and thus inhibits at an earlier stage than transglycosylation, and the inhibitors were each added after the accumulation of lipid II. Moenomycin's effects appear substantially the same as when the assay is run without the transglycosylation blocker (Triton X-100®, which also was to be expected because it is a known inhibitor of the transglycosylase-mediated reaction rather than an inhibitor of an earlier stage. The assays were performed using UDP-MurNAc-pentapeptide or alternatively UDP-MurNAc-tetrapeptide, and the results are shown in graphical form in FIGS. 2 and 3 respectively.

Figure 1:
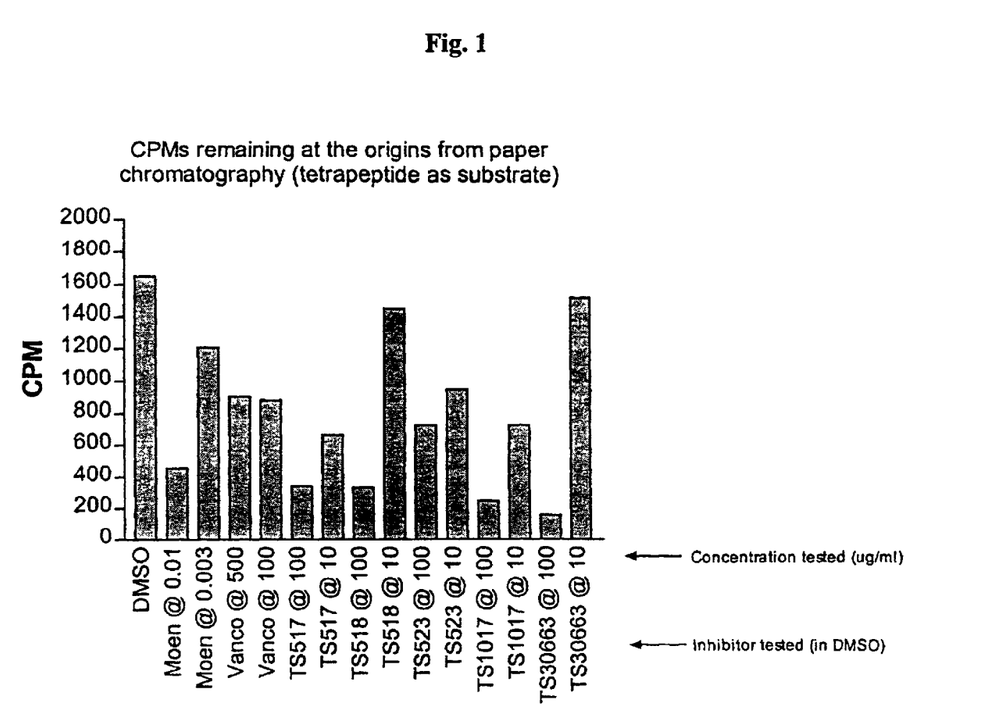
FIG. 1 is a graph showing the counts per minute (CPM) resulting from paper chromatography analysis of the results of employing the methods of this invention on several putative inhibitors.

Likewise, novel compounds synthesized at Incara Research Labs have been tested and shown to be specific for inhibiting the transglycosylation step. Compounds TS0517 (chlorobiphenyl-vancomycin), TS0518 (chlorobiphenyl-desleucyl-vancomycin), TS0523, TS1017, and TS30663 were all assayed using the above-described assay, in which the inhibitors were added to their respective samples after formation of lipid II, with the subsequent removal of Triton X-100®. After 2 hours incubation, aliquots of the solubilized products were analyzed by ascending paper chromatography. All of these compounds showed inhibition of peptidoglycan formation. The results using a variety of concentrations of the inhibitors in the assay are shown in graphical form in FIG. 1. In another assay, in which these inhibitors were added to the reaction mixture with the labeled UDP-GlcNAc and UDP-MurNAc-tetrapeptide, each of these compounds demonstrated no inhibition of lipid II formation (data not shown).

Example 4

Use of UDP-MurNAc-tetrapeptides

One may use either UDP-MurNAc pentapeptide or UDP-MurNAc tetrapeptide as the substrate for lipid I production. Using this approach, specific vancomycin-like inhibitors which bind the D-ala-D-ala peptide can be distinguished from inhibitors acting by a different mechanism. The inventors have used this approach to identify transglycosylation inhibition by novel compounds synthesized at IRL, which are known to act at a different site other than binding to the dipeptide (data not shown).

Two vancomycin derivatives, chlorobiphenyl-vancomycin (CBP-V) and chlorobiphenyl-desleucyl-vancomycin (CBP-dl-V), as well as several other compounds, were assayed using the methods of the present invention. The substrates were UDP-MurNAc-tetrapeptide and $^{14}$C labeled UDP-GlcNAc. The transglycosylation blocker Triton X-100® (0.1%) was present in the reaction mixture. Following a 10 minute incubation with UDP-MurNAc-tetrapeptide and a 1 hour incubation with $^{14}$C labeled UDP-GlcNAc, the Triton X-100® was removed and the inhibitors were added, and then peptidoglycan synthesis proceeded for a 2 hour incubation. Paper chromatography yielded results in terms of CPM, from which the $IC_{50}$ was approximated. The results are shown below in FIG. 1, wherein TS517 represents CBP-V, TS518 represents CBP-dl-V, moen represents moenomycin, and vanco represents vancomycin. Even high levels of vancomycin yielded only minimal inhibition, because there was no dipeptide moiety to which it could bind, while the derivatives CBP and CBP-dl-V were far more effective.

A separate assay was prepared to confirm this data using a variety of bacterial strains: Vancomycin-sensitive strains included E. Faecium 49624, E. Faecalis 29212, S. Aureus 29213, and S. Aureus 33591(MRSA; methicillin resistant); vancomycin-resistant strains included: E. Faecium CL4931 (VanA), E. Faecalis CL4877 (VanB). Conditions were as described above. The results, shown below in Table 2, showed that the two vancomycin derivatives were effective at inhibiting peptidoglycan synthesis in both vancomycin-sensitive and vancomycin-resistant strains.

TABLE 2

MIC of vancomycin analogs on sensitive and resistant strains.[a]

| | MIC (µg/ml)[b] | | | | | |
|---|---|---|---|---|---|---|
| Compound | E. faecium 49624 | E. faecium CL4931 (VanA) | E. faecalis 29212 | E. faecalis CL4877 (VanB) | S. aureus 29213 | S. aureus 33591 (MRSA) |
| Vancomycin | 1.25 | 1250 | 3.12 | 1250 | 1.25 | 2.5 |
| CBP-vancomycin | 0.062 | 12.5 | 0.25 | 12.5 | 0.25 | 0.25 |
| CBP-dl-vancomycin | 1.56 | 12.5 | 3.12 | 25 | 3.12 | 6.26 |
| Moenomycin | >200[c] | 0.25 | 0.078 | 0.13 | 0.05 | ND |

[a]Strains CL4931 and CL4877 are vancomycin resistant, while strain 33591 is methicillin resistant.
[b]MIC values were determined by microbroth dilution on two or more occasions with similar results.
[c]Strain 49624 appears to be naturally resistant to moenomycin.

As those skilled in the art will appreciate, numerous changes and modifications may be made to the preferred embodiments of the invention without departing from the spirit of the invention. It is intended that all such variations fall within the scope of the invention. The entire disclosure of each publication cited herein is hereby incorporated by reference.

We claim:

1. A method of assaying for transglycosylase activity comprising the steps of:

(a) incubating a reaction mixture comprising a bacterial membrane, UDP-N-acetyl-muramyl-peptide (UDP-MurNAc-peptide), labeled UDP-N-acetylglucosamine (UDP-GlcNAc), and a transglycosylation blocker;

(b) removing the transglycosylation blocker to allow labeled peptidoglycan to be synthesized; and (c) measuring said labeled peptidoglycan;

whereby the quantity of measured peptidoglycan is proportional to an amount of transglycosylase activity.

2. The method of claim 1, wherein the labeled UDP-GlcNAc is labeled with a label selected from the group consisting of a radioisotope label, a fluorescent label, a biotin label, an immunogenic label, and a chemical label.

3. The method of claim 2, wherein the radioisotope label is [14]C.

4. The method of claim 1, wherein the incubation of step (a) is performed for a period of from about 15 minutes to about 2 hours.

5. The method of claim 1, comprising the additional step of incubating the reaction mixture after the step of removing the transglycosylation blocker, for a period of from about 30 minutes to about 2 hours.

6. The method of claim 1, wherein the reaction mixture is prepared without labeled UDP-GlcNAc, incubated for a period of about 10 minutes, and then the labeled UDP-GlcNAc is added.

7. The method of claim 1, wherein the UDP-MurNAc-peptide is labeled.

8. The method of claim 1, wherein the transglycosylation blocker is a detergent.

9. The method of claim 8, wherein the detergent is a polyoxyethylene isooctylphenyl ether.

* * * * *